United States Patent [19]

Marshall et al.

[11] Patent Number: 5,391,555
[45] Date of Patent: Feb. 21, 1995

[54] METHODS FOR TREATING INFLAMMATORY BOWEL DISEASE WITH LEUKOTRIENE SYNTHESIS INHIBITORS

[75] Inventors: Paul J. Marshall, Madison; David D. Wood, Wilton; Cheryl L. Nickerson-Nutter, Milford, all of Conn.; Reiner Müller-Peddinghaus, Bergisch-Gladbach, Germany

[73] Assignee: Miles Inc., West Haven, Conn.

[21] Appl. No.: 24,199

[22] Filed: Feb. 26, 1993

Related U.S. Application Data

[63] Continuation of Ser. No. 3,253, Jan. 11, 1993, abandoned, which is a continuation of Ser. No. 790,960, Nov. 12, 1991, abandoned.

[51] Int. Cl.⁶ ............................................. A61K 31/47
[52] U.S. Cl. .................................. 514/311; 514/312; 514/314; 514/925
[58] Field of Search ................ 514/925, 311, 312, 314

[56] References Cited

U.S. PATENT DOCUMENTS 4,970,215 11/1990 Mohs et al. ........................... 514/311
5,091,392 11/1992 Raddatz et al. ....................... 514/311

FOREIGN PATENT DOCUMENTS

90/108775 3/1990 European Pat. Off. ..
92102156.4 8/1992 European Pat. Off. ..

OTHER PUBLICATIONS

Rask–Madsen et al., "5-Lipoxygenase inhibitors for the treatment of inflammatory bowel disease," Agents Action, *Special Conference Issue*, pp. C37–C46 (1992).

Wallace and Keenan, "An orally active inhibitor of leukotriene synthesis accelerates healing in a rat model of colitis," Leukotriene Inhibition in Experimental Colitis, pp. G527–G534 (1990).

Staerk Laursen et al., "Selective 5-lipoxygenase inhibition in ulcerative colitis," Lancet 335, pp. 683–685 (1990).

Okayasu et al., "A Novel Method in the Induction of Reliable Experimental Acute and Chronic Ulcerative Colitis in Mice," Gastroenterology 98, pp. 694–702 (Mar. 1990).

*Primary Examiner*—Raymond J. Henley, III
*Assistant Examiner*—T. J. Criares

[57] ABSTRACT

Described are methods for ameliorating symptoms associated with inflammatory bowel disease such as ulcerative colitis and Crohn's disease (regional enteritis) with four specific quinoline leukotriene synthesis inhibitors.

4 Claims, No Drawings

METHODS FOR TREATING INFLAMMATORY BOWEL DISEASE WITH LEUKOTRIENE SYNTHESIS INHIBITORS

This is a continuation of application U.S. Ser. No. 08/003,253, filed Jan. 11, 1993, now abandoned, which is a continuation of U.S. Ser. No. 07/790,960, filed Nov. 12, 1991, now abandoned.

FIELD OF THE INVENTION

The invention relates to methods for ameliorating symptoms associated with inflammatory bowel disease. More particularly, methods for use of four specific quinoline leukotriene synthesis inhibitors for treating ulcerative colitis and Crohn's disease (regional enteritis) are disclosed.

BACKGROUND

The clinical manifestations of ulcerative colitis and Crohn's disease share the common feature of inflammation. In ulcerative colitis the earliest lesion is an inflammatory infiltration with abscess formation at the base of the crypts of Lieberkühn. Coalescence of these distended and ruptured crypts tends to separate the overlying mucosa from its blood supply, leading to ulceration. The inflammatory involvement is diffuse and superficial, usually limited to the mucosa and submucosa.

The clinical picture includes cramping, lower abdominal pain or rectal bleeding, soon followed by frequent, loose discharges consisting mainly of blood, pus, and mucus with scanty fecal particles. The rectum and ampulla are usually found to be spastic.

In Crohn's disease (also known as regional enteritis or ulcerative ileitis) the most prominent feature of the disease is the granular, reddish-purple, edematous thickening of the bowel wall. In the early phase of the disease, the prominent irritability, spasm, and edema give the appearance of a rigid contour to the diseased segment radiogenographically.

The histological picture consists of dilated and tortuous lymph vessels and granulomatous structures which are made up predominantly of epithelioid cells, lymphocytes, and occasionally giant cells. With the development of inflammation, these granulomas often lose their circumscribed borders and merge with the surrounding tissue reaction. Obstruction is the predominant clinical feature. The stools although loose are rarely bloody.

Numerous mediators of inflammation have been demonstrated in the diseased tissue of inflammatory bowel disease. Among these are the prostaglandins and leukotrienes. Previous investigators have concluded that the inhibition of prostaglandin synthesis by cyclooxygenase inhibitors is either ineffective or contra-indicated for the treatment of inflammatory bowel disease. In contrast, the inhibition of leukotriene synthesis appears to be clinically beneficial.

Leukotrienes belong to a family of biomolecules called eicosanoids. Eicosanoids are derived from arachidonic acid and are classified according to their derivative enzymatic pathways, for instance, cyclooxygenase products which include prostaglandins, thromboxanes and prostacyclins; 15-lipoxygenase products, which include lipoxins; and 5-lipoxygenase products, which include the leukotrienes (LTA4, LTB4, LTC4, LTD4, and LTE4).

It has been known that leukotrienes have a role in allergic and inflammatory diseases. For instance, LTC4, LTD4 and LTE4 were previously referred to collectively as the slow-reacting substance of anaphylaxis (Morris et al., 1980, Nature, 285:104–106). Leukotrienes affect microvascular function by increasing hemodynamic margination of leukocytes, promoting permeability at postcapillary venules and eliciting leukocyte diapedesis, all leading to focal formation of interstitial inflammation.

Extravascular infiltration begins with adherence of leukocytes to the postcapillary venular endothelium. LTB4 and LTC4 can increase the adhesiveness of leukocytes to endothelial cells. LTC4, LTD4 and LTE4 can contract adjacent endothelial cells which increases permeability of venules.

LTB4 effects neutrophil chemotaxis, chemokinesis, aggegation, lysozyme release, superoxide production and augmentation of complement-dependent cytotoxicity. LTB4 also effects eosinophil, macrophage and monocyte chemotaxis and chemokinesis, and in lymphocytes increases cytotoxicity.

Evidence for the involvement of leukotrienes in the pathology of inflammatory bowel disease has accumulated over the last several years. For example, the ability of the mucosal tissue to synthesize LTB4 and the peptidoleukotrienes (LTC4, LTD4, and LTE4) are substantially elevated in both Crohn's disease and in ulcerative colitis (Sharon et al., 1984, Gastroenterol, 86:453–460; Dreyling et al., 1986, Biochim Biophys Acta, 878:184–193; Peskar et al., 1986, Agents Actions, 18:381–383).

Moreover, a positive correlation exists between the luminal concentration of LTB4 and the disease activity judged by clinical, endoscopic or histological gradings in ulcerative colitis (Lauritsen, et al., 1989, Gastroenterol, 91:837–844). The biological activities of the leukotrienes also support the hypothesis for a role in inflammatory bowel disease. The peptidoleukotrienes cause vascular permeability which may contribute to the tissue edema seen in both Crohn's disease and in ulcerative colitis (Hua, et al., 1985, Naunyn-Schmeideberg's Arch Pharmacol., 330:136–141).

Peptidoleukotrienes also contract intestinal smooth muscle (Cristol et al., 1988, Res Commun Chem Pathol Pharmacol., 59:423–426) and stimulate ion secretion from the ileum (Smith et al., 1988, Am J Physiol., 255:G175–183) and colonic mucosa (Jett et al., 1991, J Pharmacol Exp Therap. 257:698–705), which may contribute to the diarrhea associated with the intestinal inflammation.

Finally, LTB4 is the major chemotactic agent for neutrophils and macrophages found in the mucosal extracts of ulcerative colitis patients (Lobos et al., 1987, Dig. Dis. Sci., 32:1380–1388), which could account for the cellular infiltration.

SUMMARY OF THE INVENTION

The present invention utilizes the following specific, optically active, quinoline derivatives to inhibit the synthesis of leukotrienes, which has a therapeutic effect on mediating the pathology associated with inflammatory bowel disease:

R-(−)-2-cyclopentyl-2-[4-(2-quinolinyl-methoxy)-phenyl]-acetic acid;

R-(−)-2-cycloheptyl-N-methylsulfonyl-2-[4-(2-quinolinyl-methoxy)phenyl]-acetamide;

(−)-2-cycloheptyl-2-[3-isobutyl-4-(2-quinolinyl-methoxy)-phenyl]-acetic acid; and (−)-2-hydroxy-2-(2-indanyl)-2-[4-(2-quinolinyl-methoxy)-phenyl]-acetic acid.

DETAILED DESCRIPTION

Synthesis of R-(−)-2-cyclopentyl-2-[4-(2-quinolinyl-methoxy)-phenyl]-acetic acid (Formula I, above) is disclosed in U.S. Pat. No. 4,970,215.

Synthesis of R-(−)-2-cycloheptyl-N-methylsulfonyl-2-[4-(2-quinolinyl-methoxy)-phenyl]-acetamide (Formula II, above) is disclosed in U.S. Pat. No. 5,091,392.

Synthesis of (−)-2-cycloheptyl-2-[3-isobutyl-4-(2-quinolinyl-methoxy)-phenyl]-acetic acid (Formula III, above) is disclosed in European Patent Application No. 92/102156.4.

Synthesis of (−)-2-hydroxy-2-(2-indanyl)-2-[4-(2-quinolinyl-methoxy)-phenyl]-acetic acid (Formula IV, above) is disclosed in U.S. patent application No. 934,059.

Several structural classes of compounds have been identified as inhibitors of leukotriene synthesis based primarily upon their ability to inhibit the production of LTB4 by human neutrophils stimulated with the calcium ionophore A23187 (Gillard et al, 1989, Can J Physiol J Pharmacol Exp Therap. 256:929; Carter et al., 1991, Pharmacol, 67:456). Since leukotrienes have been implicated in numerous inflammatory disease states including asthma, rhinitis, inflammatory arthritis, psoriasis, and inflammatory bowel disease, it has been generally assumed, prior to this disclosure, that the activity of a particular leukotriene synthesis inhibitor correlates with its activity as an inhibitor of the synthesis of LTB4 by human neutrophils in blood.

Recently, it was reported that the activity of R-(−)-2-cyclopentyl-2-[4-(2-quinolinyl-methoxy)-phenyl]-acetic acid (Formula I, above) as a bronchodilator in man is considerably greater than would have been predicted from the degree of inhibition of neutrophil-dependent LTB4 synthesis which would have been achieved by the concentration of the drug in the blood.

It has now been discovered that the activity of leukotriene synthesis inhibitors (hereinafter "LSI") in inflammatory bowel disease correlates with their activity on human bronchial muscle and not with their activity associated with neutrophil LTB4 synthesis.

To evaluate the correlation with bronchial smooth muscle activity, the following study was conducted:

EXAMPLE 1

For evaluation of the response of human blood polymorphonuclear leukocytes (PMN), 0.5 ml aliquots of human blood with heparin as the anticoagulant are preincubated for 10 minutes with 2 μl dimethylsulfoxide (DMSO) alone or with DMSO containing the compound to be tested (shaken in water bath at 37° C.).

The PMN are then stimulated with a final concentration 30 μM of the ionophore A23187 for 30 minutes at 37° C. The reaction is terminated with 1 ml methanol. The incubate is cooled 20 minutes in an ice bath, vortexed, then centrifuged at 13,000 g.

The amount of LTB4 present in the removed supernatant is analysed by HPLC and/or radioimmune assays.

For the measurement of human bronchial muscle contraction, bronchial rings were obtained from patients undergoing surgical resection of the lungs typical for lung cancer. The muscle rings were set up in organ baths under an initial load of 3 g and contracted with 100 μM acetylcholine in Tyrode's solution to provide a standardized contraction. The organs were then washed until they returned to the baseline tension in Tyrode's solution containing atropine 1 μM, indomethacin 3 μM and polaramine 1 μM at 37° C.

Contraction was stimulated by the treatment of the muscle strips with anti-human IgE (1/1000) with or without LSI. The intensity of the contractions were expressed as the percentage of the acetylcholine-induced contraction. The percentage of inhibition by the LSI was calculated from the ratio of the relative contractions. The activity of several of the well known LSIs of other structural classes (Zileuton & MK886) are compared below with the quinolines of the present invention.

TABLE 1

| Test Substance | $ED_{50}$ ($\mu M$) human whole blood | $ED_{50}$ ($\mu M$) human bronchial muscle |
|---|---|---|
| MK886 | 0.43 | 0–39% @ $\mu M$ |
| Zileuton | 0.69 | 4.0% @ 1 $\mu M$ |
| Formula II | 1.1 | 0.8 |
| Formula III | 3.0 | 1.0 |
| Formula IV | 4.5 | 0.1 |
| Formula I | 17.0 | 0.8 |

Where:

Formula I is R-(−)-2-cyclopentyl-2-[4-(2-quinolinyl-methoxy)-phenyl]-acetic acid.

Formula II is R-(−)-2-cycloheptyl-N-methylsulfonyl-2-[4-(2-quinolinyl-methoxy)-phenyl]-acetamide.

Formula III is (−)-2-cycloheptyl-2-[3-isobutyl-4-(2-quinolinyl-methoxy)-phenyl]-acetic acid.

Formula IV is (−)-2-hydroxy-2-(2-indanyl)-2-[4-(2-quinolinyl-methoxy)-phenyl]-acetic acid.

Efficacy was demonstrated in the following three animal models:

EXAMPLE 2

Mouse Ear Inflammation Test

Because it is known that leukotrienes are the major mediators of the edema which follows the application of arachidonic acid on the skin of the mouse ear and because the human clinical trials have implicated leukotrienes in the pathology of Inflammatory Bowel Disease (IBD), the mouse ear inflammation test can be used as a model to predict efficacy in IBD.

In this test edema is induced by the topical application of 10 μl of a 20% arachidonic acid solution on the mouse ear. 60 minutes before arachidonic acid application the animals were treated orally with compound or vehicle. 30 minutes after the induction of inflammation the swelling of the ear was measured. The results averaged over several experiments are shown below.

TABLE 2

| Test Substance | Edema formation - $ED_{50}$ (mg/kg) |
|---|---|
| Zileuton | 47.4 |
| Formula I | 48.7 |
| Formula II | 5.2 |
| Formula III | 12.5 |
| Formula IV | 15.0 |
| MK886 | ca.100 |

Where:

Formula I is R-(−)-2-cyclopentyl-2-[4-(2-quinolinyl-methoxy)-phenyl]-acetic acid.

Formula II is R-(−)-2-cycloheptyl-N-methylsulfonyl-2-[4-(2-quinolinyl-methoxy)-phenyl]-acetamide.

Formula III is (—)-2-cycloheptyl-2-[3-isobutyl-4-(2-quinolinyl-methoxy)-phenyl]-acetic acid.

Formula IV is (—)-2-hydroxy-2-(2-indanyl)-2-[4-(2-quinolinyl-methoxy)-phenyl]-acetic acid.

EXAMPLE 3

TNBS-induced colitis in rats.

A colitis resembling human ulcerative colitis can be induced in rats by the intracolonic infusion of trinitrobenzene sulfonic acid (Wallace et al., 1990, Am J Physiol. 258:G527–34).

Male Wistar rats were lightly anesthetized with ether, and a 2.3 mm rubber cannula inserted into the lumen of the colon via the anus. The cannula was advanced so that the tip was approximately 8 cm proximal to the anus. Colitis is induced by the administration of 0.25 ml of 50% ethanol (vol/vol) containing 30 mg of 2,4,6-trinitrobenzene sulfonic acid (TNB) through the cannula. After instilling the TNB-ethanol solution, the cannula was left in place for a few seconds then gently removed.

Animals were sacrificed at various time intervals after the administration of TNB-ethanol for examination of the level of LTB4 in the tissue and for histological examination.

R-(—)-2-cyclopentyl-2-[4-(2-quinolinyl-methoxy)-phenyl]-acetic acid, at doses of 30 and 100 mg/kg or placebo is administered orally to these animals bid beginning 2 hours before induction of colitis and continuing for the next 7 days. Two hours after the administration of the test compound, animals are sacrificed and samples of the grossly inflamed colonic tissue are excised and incubated in vitro for 20 minutes.

Analysis of the culture supernatants shows that the synthesis of LTB4, but not of TxB2, is markedly inhibited by the pretreatment with R-(—)-2-cyclopentyl-2-[4-(2-quinolinyl-methoxy)-phenyl]-acetic acid.

The remaining animals after completion of the drug treatment are maintained for an additional 7 days before sacrifice in order to examine the colonic damage. In the placebo treated animals 14 days following the induction of colitis, adhesions are present and multiple sites of ulceration are found often extending transmurally through the mucosa.

Treatment with R-(—)-2-cyclopentyl-2-[4-(2-quinolinyl-methoxy)-phenyl]-acetic acid, reduces both the frequency of adhesions and the frequency and extend of the ulcerations.

EXAMPLE 4

Dextran Sulfate-induced colitis in mice.

Mice, when provided 5% high molecular weight dextran sulfate in their drinking water for 5–7 days, develop an acute colitis with diarrhea, gross rectal bleeding, and weight loss (Okayasu et al., 1990, Gastroenterol, 98:694–702). The large intestine of these animals exhibits multiple erosions and inflammatory changes.

In this model, the administration of: R-(—)-2-cycloheptyl-N-methylsulfonyl-2-[4-(2-quinolinyl-methoxy)-phenyl]-acetamide, at doses of 10 mg/kg or 30 mg/kg orally bid resulted in a decrease in the symptoms of colitis including a reduction in weight loss, an improvement in stool consistency, and a reduction in occult blood in the stool.

What is claimed is:

1. A method of treating inflammatory bowel disease in a mammal suffering therefrom comprising administering a therapeutically effective amount of R-(—)-2-cyclopentyl-2-[4-(2-quinolinyl-methoxy)-phenyl]-acetic acid.

2. A method of treating inflammatory bowel disease in a mammal suffering therefrom comprising administering a therapeutically effective amount of R-(—)-2-cycloheptyl-2-N-methylsulfonyl-2-[4-(2-quinolinyl-methoxy)-phenyl]acetamide.

3. A method of treating inflammatory bowel disease in a mammmal suffering therefrom comprising administering a therapeutically effective amount of R-(—)-2-cyclopentyl-2-[3-isobutyl-4-(2-quinolinyl-methoxy)-phenyl]-acetic acid.

4. A method of treating inflammatory bowel disease in a mammal suffering therefrom comprising administering a therapeutically effective amount of (—)-2-hydroxy-2-(2-indanyl)-2-[4-(2-quinolinyl-methoxy)-phenyl]-acetic acid.

* * * * *